(12) United States Patent
Fournial et al.

(10) Patent No.: US 8,603,498 B2
(45) Date of Patent: Dec. 10, 2013

(54) LIPO-PHOSPHATED OR LIPO-SULPHATED COMPOUND, COMPOSITIONS COMPRISING IT AND TOPICAL USES THEREOF

(75) Inventors: Arnaud Fournial, Paris (FR); Philippe Mondon, Cachan (FR); Olivier Peschard, Saint Prest (FR)

(73) Assignee: Sederma, S.A.S., Le Perray en Yvelines (FR)

( * ) Notice: Subject to any disclaimer, the term of this patent is extended or adjusted under 35 U.S.C. 154(b) by 0 days.

(21) Appl. No.: 13/522,663

(22) PCT Filed: Jan. 17, 2011

(86) PCT No.: PCT/IB2011/050196
§ 371 (c)(1),
(2), (4) Date: Aug. 28, 2012

(87) PCT Pub. No.: WO2011/086532
PCT Pub. Date: Jul. 21, 2011

(65) Prior Publication Data
US 2013/0004439 A1    Jan. 3, 2013

(30) Foreign Application Priority Data
Jan. 18, 2010  (FR) ..................... 10 50306

(51) Int. Cl.
*A61K 9/00*   (2006.01)
*A61K 8/02*   (2006.01)

(52) U.S. Cl.
USPC .......................... 424/400; 424/401

(58) Field of Classification Search
USPC ................. 424/400, 401
See application file for complete search history.

(56) References Cited

U.S. PATENT DOCUMENTS

| | | | |
|---|---|---|---|
| 4,150,069 A * | 4/1979 | Crutchfield et al. | 558/180 |
| 5,260,051 A * | 11/1993 | Cho | 424/57 |
| 6,384,022 B1 | 5/2002 | Jackson et al. | |
| 2005/0085537 A1* | 4/2005 | Rao et al. | 514/517 |

FOREIGN PATENT DOCUMENTS

| | | | |
|---|---|---|---|
| JP | 08239622 | | 9/1996 |
| JP | 08239622 A | * | 9/1996 |
| WO | WO 03/103625 | | 12/2003 |
| WO | WO 2004103265 A2 | * | 12/2004 |

OTHER PUBLICATIONS

Friedkin, M.; Lehninger, A.L. The Synthesis of Phosphomalic Acid. Mar. 31, 1947. Journal of Biological Chemistry. 169 (1), 183-90.*
International Search Report dated Apr. 26, 2011 for PCT/IB2011/050196.
Tanojo, Hanafi et al. "In Vitro Human Skin Barrier Modulation by Fatty Acids: Skin Permeation and Thermal Analysis Studies," *Pharmaceutical Research*, 14:1 (Jan. 1, 1997) 42-49.

* cited by examiner

*Primary Examiner* — Sean Basquill
*Assistant Examiner* — Andrew S Rosenthal
(74) *Attorney, Agent, or Firm* — Jones Day

(57) ABSTRACT

The compound according to the invention has the following developed formula IX:

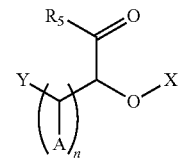

wherein:
X=$PO(OH)_2$; $SO_2(OH)$; $PO(OH)(Xaa)_m$ or $SO_2(Xaa)_m$;
A=H; OH; $NH_2$ or akyl (1-6C);
n=1 to 4;
Y=—CO—$OR_2$;   —CO—$NR_3R_4$;   —O—CO—$R_2$;   —C≡$CR_2$;
$R_2$=an alkyl, aryl, aralkyl, acyl, sulfonyl, sugar or alkoxy chain of 1 to 24 carbon atoms, linear, branched or cyclic, with or without substitutions, saturated or not, hydroxylated or not, sulfurated or not;
$R_5$=OH, O-alk (1-6C), $(Xaa)_m$, $NH_2$ or NH-alkyl(1-6C);
Xaa=peptide of m aminoacids Xaa with m from 1 to 10;
The compound is preferably phosphated, obtained from malic acid and having the following developed formula:

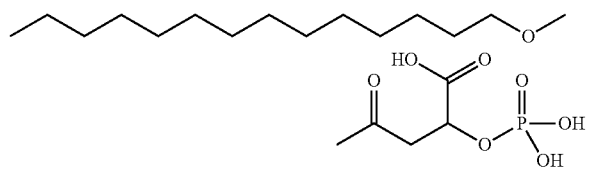

A cosmetic composition comprising the compound of the present invention can improve the general condition of the skin, for example hydration, lightening and mechanical properties.

16 Claims, No Drawings

LIPO-PHOSPHATED OR LIPO-SULPHATED COMPOUND, COMPOSITIONS COMPRISING IT AND TOPICAL USES THEREOF

CROSS REFERENCE TO RELATED APPLICATION

This application is the National Phase application of International Application No. PCT/IB2011/050196, filed Jan. 17, 2011, which designates the United States and was published in English. The foregoing related application, in its entirety, is incorporated herein by reference.

TECHNICAL FIELD

The subject matter of the present invention is a new sulphated or phosphated lipidic compound, a composition comprising it and uses thereof, for example in the field of cosmetics, personal care products and dermopharmacy.

The present invention concerns the chemical, medical or cosmetical industries for the care of the skin and appendages (such as hair, eyelashes, eyebrows, nails, hairs) of mammals, animals or humans.

BACKGROUND ART

The cosmetics industry is constantly looking for new active compounds to propose for formulating new cosmetic products. Increasingly, compounds are sought which must be active on several targets to improve the overall condition of the skin, that is to say at first its degree of hydration, but also its mechanical properties and/or also its brightness. Also, a new active ingredient can be sought that is most specific, able to beautify the skin and appendages, such as by adding volume, clarifying the complexion, slimming, etc.

The object of the present invention is to meet this demand.

SUMMARY OF THE INVENTION

To this aim, a compound of the following developed formula I is proposed:

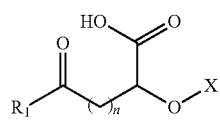

$R_1$ being a lipidic/lipophilic chain
$X=PO(OH)_2$ or $SO_2(OH)$
n=1 to 4.

The present invention is therefore aiming the two following types of compounds:

The phosphated compounds having the following developed formula II:

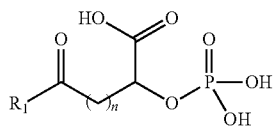

The sulphated compounds having the following developed formula III:

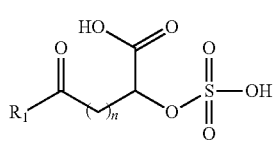

According to the invention, a lipidic/lipophilic chain $R_1$ is recited as being $R_1=OR_2$ or $NR_3R_4$.

$R_2$ is an alkyl, aryl, aralkyl, acyl, sulfonyl, sugar or alkoxy chain of 1 to 24 carbon atoms, preferably of at least 4 carbon atoms, linear, branched or cyclic, with or without substitutions, saturated or not, hydroxylated or not, sulfurated or not.

$R_3$ and $R_4$ are, independently from each other, either a hydrogen or a $R_2$ chain, namely an alkyl, aryl, aralkyl, acyl, sulfonyl, sugar or alkoxy chain of 1 to 24 carbon atoms, preferably of at least 4 carbon atoms, linear, branched or cyclic, with or without substitutions, saturated or not, hydroxylated or not, sulfurated or not, one of $R_3$ and $R_4$ being an $R_2$ type chain.

The compounds according to the present invention can be used in the form of salts or acids or a mixture of both depending on the pH of use.

In vitro and in vivo test results were obtained with the compounds according to the invention leading to a high potential of applications in cosmetics or dermopharmacy.

According to preferred features:
$R_1=OR_2$ with $R_2$=hydrocarbon chain having at least 4 carbon atoms and/or
the compound of the invention is phosphated X being $PO(OH)_2$ and/or
n=1

More preferably, the compound of the present invention is obtained from malic acid or from one of its derivatives or analogs as starting material.

Thus, a preferred compound according to the invention is the 2-phosphate-succinic-acid-4-tetradecyle ester having the following developed formula IV and called thereafter in the text the <<Lipo-Phosphomalate>>:

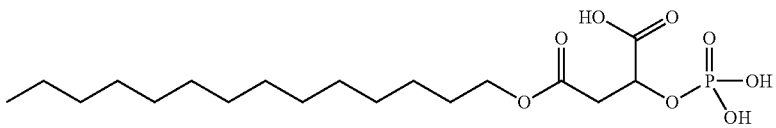 [SMILES: CCCCCCCCCCCCCCOC(=O)CC(OP(=O)(O)O)C(=O)O]

with n=1, $X=PO(OH)_2$ and $R_1=OC_{14}H_{29}$.

The use of the malic acid as one of the starting materials leads advantageously to a manufacture process that is simple and presenting a height yield as described below.

Other commercial diacids are advantageously suitable to obtain the compound of the invention, for example tartaric acid (the 2,3-dihydroxybutanedioic acid) of following developed formula V:

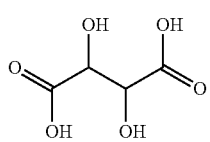

According to further features:

The compound can comprise a substitution on the —(CH$_2$)$_n$-chain, for example chosen among OH, NH$_2$ or an alkyl chain; preferably a lower alkyl chain and/or The carbonyl function can be replaced by a double bound analog function as disclosed in the following developed formula VI:

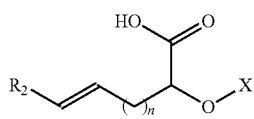

And/or the COOH carboxylic acid function of the compound of the invention can be present in a derivated form, for example an ester form.

Advantageously, the compound of the invention can be coupled with any peptide of m aminoacids Xaa with m from 1 to 10 for obtaining a compound of the following developed formula VII, the coupling being achieved through a peptidic type bond with the COOH of the compound according to the invention:

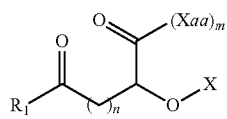

And/or with one OH of the X substituent.

The compound of the invention becomes thus a phosphated or sulfated alternative to the classical lipidic chains coupled to peptides, like a palmitoyle, elaidoyle or biotinoyle chain, the lipidic or lipophyle R1 having the function to improve the bioavailability of the peptide and its cutaneous penetration ability.

The invention encompasses peptides (Xaa)$_m$ consisting of encoded, natural or unnatural, derivatives and analogs amino acids (coded aminoacids: Alanine A Ala, Arginine R Arg, Asparagine N Asn, Aspartate ou aspartic acid D Asp, Cystein, C Cys, Glutamate ou glutamic acid E Glu, Glutamine Q Gln, Glycine G Gly, Histidine H His, Isoleucine I Ile, Leucine L Leu, Lysine K Lys, Methionine M Met, Phenylalanine F Phe, Proline P Pro, Serine S Ser, Threonine T Thr, Tryptophane W Trp, Tyrosine Y Tyr, Valine, V Val). Are cited for example, without being restrictive, the aminoacids K, T, C, M, MO (methionine whose sulfur is oxydated), MO$_2$ (methionine whose sulfur is dioxydated sulfur), the dipeptides KT, KC, KP, VW, KK, TT, YR, NF, DF, EL, CL, AH, YR, carnitine, the tripeptides RKR, HGG, GHK, GKH, GGH, GHG, KFK, GKH, KPK, KMOK, KMO2K, KAvaK, the tetrapeptides RSRK (SEQ ID NO:1), GQPR (SEQ ID NO:2) or KTFK (SEQ ID NO:3), the pentapeptides KTTKS (SEQ ID NO:4), the hexapeptides GKTTKS (SEQ ID NO:5), VGVAPG (SEQ ID NO:6), etc.

As for other example, the aminoacid sequences of the following marketed peptides can be mentioned as well: Vialox™, Syn-ake™ or Syn-Coll™ (Pentapharm), Hydroxyprolisilane CN™ (Exsymol), Argireline™, Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), Cytokinol™LS (Laboratoires Serobiologiques/Cognis), Kollaren™, IP2000™ or Meliprene™ (Institut Europeen de Biologie Cellulaire), Neutrazen™ (Innovations), ECM-Protect™ (Atrium Innovations), Timp-Peptide™ or ECM Moduline™ (Infinitec Activos), as well as the peptides mentioned thereafter in the text.

Beyond ten amino acids, derivatives or analogs of amino acids, the peptides are generally too bulky for cosmetic applications and too expensive to manufacture. For these reasons, the coupled peptide is preferably limited to n=6 (hexapeptide).

It is also possible that the compound according to the invention be a bis-lipo sulphated or bis- or tri phosphated. The following developed formula VIII illustrates this characteristic of the invention as for example for a compound according to the invention that is bis-lipo phosphated:

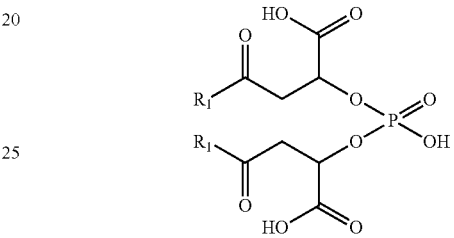

The compound of the present invention can be represented by the following general formula IX incorporating all the possible variants disclosed above:

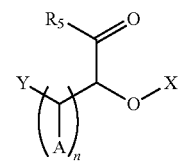

Wherein:

X=PO(OH)$_2$; SO$_2$(OH); PO(OH)(Xaa)$_m$ or SO$_2$(Xaa)$_m$;

A=H; OH; NH$_2$ or akyl (1-6C);

n=1 to 4;

Y=—CO—OR$_2$; —CO—NR$_3$R$_4$; —O—CO—R$_2$; —C=CR$_2$;

R$_2$=an alkyl, aryl, aralkyl, acyl, sulfonyl, sugar or alkoxy chain of 1 to 24 carbon atoms, linear, branched or cyclic, with or without substitutions, saturated or not, hydroxylated or not, sulfurated or not; preferably a chain of at least 4 carbons;

R$_3$ and R$_4$ are, independently from each other, either a hydrogen atom or a R$_2$ chain;

R$_5$=OH, O-alk (1-6C), (Xaa)$_m$, NH$_2$ or NH-alkyl(1-6C);

Xaa=peptide of m aminoacids Xaa with m from 1 to 10.

In the developed formula I,

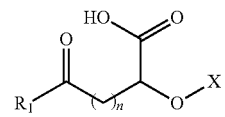

X=PO(OH)$_2$ or SO$_2$(OH)

R$_5$=OH

A=H n=1 to 4,

Y=—CO—R$_1$ with R$_1$=OR$_2$ or NR$_3$R$_4$.

The object of the present invention is also a topical composition, cosmetic or dermopharmaceutical, characterized in that it comprises the compound as recited above in a physiologically acceptable medium, the use of this composition in cosmetic or dermopharmacy to improve the general condition of the skin, for example to treat the intrinsic and extrinsic cutaneous signs of ageing, to treat skin sagging, to improve the tonicity, firmness, elasticity of skin, to treat cutaneous atrophy, to improve the density of the dermis and epidermis, to treat cutaneous dehydration, to treat hair loss, to stimulate the expansion of adipose tissues, to lighten the skin, for treating glycation of molecules in the skin, to treat acne, to treat skin degradation due to the effects of oxidation and to treat inflammatory conditions.

Therefore, applications can be offered in ranges including moisturizers, cleansers, anti-aging, antioxidant, protective, restorative (hands, feet, lips), outlines (face, eyes, neck, lips), makeup care for the skin and its appendages, including eyelashes, lip products, solar products, remodeling, plumping, refiling (eg of the hands, bust, breasts), hair care, etc.

More particularly, in-vitro and in-vivo test results given in the detailed description show that the composition is useful for preventing or treating the cutaneous signs of ageing, preventing or treating cutaneous dehydration, for improving the suppleness of skin, for treating the loss of firmness, for treating fine lines and wrinkles, for stimulating the expansion of adipose tissue and for lightening the skin.

According to other advantageous features, the cosmetic or dermopharmaceutical composition of the invention may incorporate one or more additional active ingredients, to provide advantageously a cosmetic or dermo-pharmaceutical product with a wider range of properties or to enhance the properties of the compounds of the present invention. Additional active ingredients may for example be selected from the lightening, anti-redness, sunscreens, moisturizing, humectants, exfoliating, anti-aging, anti-wrinkle and fine lines, stimulating the collagen and/or elastin synthesis, volumizing, elastic properties improving, anti-acne, anti-inflammatory, anti-oxidants, anti-free radical, or propigmenting depigmenting agents, depilatories, anti-regrowth or promoting the growth agents, peptides, vitamins etc. These active ingredients may be obtained from plant materials such as plant extracts or products from plant cells culture or fermentation.

More specifically, the compound of the invention can be combined with at least one of compounds selected from compounds of vitamin B3, niacinamide compounds like or tocopherol, retinol, hexamidine, α-lipoic acid, resveratrol or DHEA or N-acetyl-Tyr-Arg-O-hexadecyl, Pal-VGVAPG (SEQ ID NO:7), Pal-KTTKS (SEQ ID NO:8), Pal-GHK, Pal-KMO2K and Pal-GQPR (SEQ ID NO:9) peptides, which are active ingredients used in conventional cosmetic or dermopharmaceutical topical compositions.

DETAILED DESCRIPTION

The term "physiological medium" means according to the present invention, without limitation, an aqueous or alcoholic solution, a water-in-oil emulsion, an oil-in-water emulsion, a microemulsion, an aqueous gel, an anhydrous gel, a serum, a dispersion of vesicles.

"Physiologically acceptable" means that the disclosed compositions or compounds are suitable for use in contact with mucous membranes, nails, scalp, hairs, hair and skin of mammals and more particularly human without risk of toxicity of incompatibility, instability, allergic response, and others.

When present in a composition, the compound of the invention is present in amounts ranging from 0.000001% to 15% compared to the total weight of the composition, more preferably between 0.0001% and 5%, depending of the destination of the composition and the desired effect more or less pronounced.

All percentages and ratios used herein are by weight of total composition and all measurements are made at 25° C. unless it is specified otherwise.

Typically, in a composition of the invention consisting simply of the compound of the invention and of an excipient (the physiologically medium) used as solubilizer, for example, forming an "active ingredient" for the future preparation of a cosmetic composition, the amount of the compound will be comprised between 0.00005% and 0.05%.

The choice of the excipient of the composition is made according to the constraints related to the compounds of the invention (stability, solubility, etc.) and if according to the dosage form then considered for the composition.

The compounds of the invention have solubility in water that varies according to their exact chemical nature. Thus the compounds of the invention can be incorporated into compositions using an aqueous solution, and those that are not soluble in water can be solubilized with cosmetically, pharmaceutically or physiologically acceptable conventional solubilizers, for example and without limiting this list: ethanol, propanol, isopropanol, propylene glycol, glycerin, butylene glycol, or polyethylene glycol or any combination. It may also be interesting to dissolve the compounds of the invention using emulsifiers and for example emulsifiers containing phosphorus such as phosphate esters.

Additional Ingredients

The CTFA International cosmetic ingredient dictionary & handbook (13th Ed. 2010) (published by the Cosmetic, Toiletry, and Fragrance Association, Inc., Washington, D.C.) describes a non limited wide variety of cosmetic and pharmaceutical ingredients usually used in the skin care industry that can be used as additional ingredients in the compositions of the present invention. Examples of these ingredient classes include, but are not limited to: healing agents, skin anti-aging agents, anti-wrinkle agents, anti-atrophy agents, skin moisturizing agents, skin smoothing agents, antibacterial agents, pesticides anti parasitic agents, antifungal agents, fungicidal agents, fungistatic agents, bactericidal agents, bacteriostatic agents, antimicrobial agents, anti-inflammatory agents, antipruriginous agents, external anesthetic agents, antiviral agents, keratolytic agents, free radicals scavengers, antiseborrheic agents, antidandruff agents, the agents modulating the differentiation, proliferation or pigmentation of the skin and agents accelerating penetration, desquamating agents, melanin synthesis stimulating or inhibiting agents, whitening or depigmenting agents, propigmenting agents, self-tanning agents, NO-synthase inhibiting agents, antioxidants, free radical scavengers and/or agents against atmospheric pollution, reactive carbonyl species scavengers, antiglycation agents, tightening agents, agents stimulating the synthesis of dermal or epidermal macromolecules and/or capable of inhibiting or preventing their degradation, such as for example collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, aquaporin synthesisstimulation agents, hyaluronic acid synthesis-stimulating agents, fibronectin synthesis-stimulating agents, sirtuin synthesis-stimulating agents, agents stimulating the synthesis of lipids and components of the stratum corneum (ceramides, fatty acids, etc.), agents that inhibit collagen degradation, other agents that inhibit elastin degradation, agents that inhibit serine proteases such cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, antihyperkeratosis agents, comedolytic agents, antipsoriasis agents, DNA repair agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, muscle relaxants; antipollution and/or anti-free radical agents; lipolytic agents, venotonic agents, slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, chelating agents, plant extracts, plant derivatives, plant tissue extracts, plant seed extracts, plant oils, botanicals, botanical extracts, essential oils, marine extracts, agents obtained from a biofermentation process, mineral salts, cell extracts and sunscreens (organic or mineral photoprotective agents active against ultraviolet A and/or B rays), ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, and vitamins and derivatives thereof, peeling agents, moisturizing agents, curative agents, lignans, preservatives, UV absorbers, a cytotoxic, an antineoplastic agent, a fat-soluble active, suspending agents, viscosity modifiers, dyes, nonvolatile solvents, diluents, pearlescent aids, foam boosters, a vaccine, and their mixture.

The additional ingredient can be selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, KTTKS (SEQ ID NO:4), PalKTTKS (SEQ ID NO:8), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, biotin, amino acids and their salts and derivatives, water soluble amino acids, asparagine, alanine, indole, glutamic acid, water insoluble vitamins, vitamin A, vitamin E, vitamin F, vitamin D, mono-, di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, pal-GHK, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoïdes, ceramides and pseudo-ceramides, a lipid complex, oils in general of natural origin such shea butter, apricot oil, onagre oil, prunus oil, palm oil, monoi oil, HEPES, procysteine, O-octanoyl-6-D-maltose, the disodium salt of methylglycinediacetic acid, steroids such as diosgenin and derivatives of DHEA, DHEA or dehydroepiandrosterone and/or a precursor or chemical or biological derivative, N-ethyloxycarbonyl-4-para-aminophenol, bilberry extracts; phytohormones; extracts of the yeast *Saccharomyces cerevisiae*, extracts of algae, extracts of soyabean, lupin, maize and/or pea, alverine and its salts, in particular alverine citrate, extract of butcher's broom and of horse chestnut, and mixtures thereof, a metallopreoteinase inhibitor. Further skin care and hair care active ingredients that are particularly useful can be found in SEDERMA commercial literature and on the website www.sederma.fr.

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

The following known actives can be mentioned, as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Essenskin™ (Sederma), Moist 24™ (Sederma), Argireline™ (trade name of the acetyl hexapeptide-3 of Lipotec), spilanthol or an extract of *Acmella oleracea* known under the name Gatuline Expression™ (EP 1722864), an extract of *Boswellia serrata* known under the name Boswellin™, Deepaline PVB™ (Seppic), Syn-AKE™ (Pentapharm), Ameliox™, Bioxilift™ (Silab) or mixtures thereof Among other plant extracts which can be combined with the compound of the invention, there may more particularly be mentioned extracts of Ivy, in particular English Ivy (*Hedera Helix*), of Chinese thorowax (*Bupleurum chinensis*), of *Bupleurum Falcatum*, of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria* L), of big-flowered Jarva tea (*Orthosiphon Stamincus* Benth), of algae (*Fucus Vesiculosus*), of birch (*Betula alba*), of green tea, of cola nuts (*Cola Nipida*), of horse-chestnut, of bamboo, of spadeleaf (*Centella asiatica*), of heather, of fucus, of willow, of mouse-ear, of escine, of cangzhu, of *chrysanthellum indicum*, of the plants of the *Armeniacea* genus, *Atractylodis Platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Centella asiatica* and *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum* extract (*Kava Kava* from SEDERMA (FR 2 771 002 and WO 99/25369), *Bacopa monieri* extract (Bacocalmine™ from SEDERMA, WO 99/40897) and sea whip extract, extracts of *Glycyrrhiza glabra*, of mulberry, of *melaleuca* (tea tree), of *Larrea divaricata*, of *Rabdosia rubescens*, of *euglena gracilis*, of *Fibraurea recisa Hirudinea*, of *Chaparral Sorghum*, of sun flower extract, of *Enantia chlorantha*, of Mitracarpe of *Spermacocea* genus, of *Buchu barosma*, of *Lawsonia inermis* L., of *Adiantium Capillus-Veneris* L., of *Chelidonium majus*, of *Luffa cylindrical*, of Japanese Mandarin (*Citrus reticulata Blanco* var. *unshiu*), of *Camelia sinensis*, of *Imperata cylindrical*, of *Glaucium Flavum*, of *Cupressus Sempervirens*, of *Polygonatum multiflorum*, of *loveyly hemsleya*, of *Sambucus Nigra*, of *Phaseolus lunatus*, of *Centaurium*, of *Macrocystis Pyrifera*, of *Turnera Diffusa*, of *Anemarrhena asphodeloides*, of *Portulaca pilosa*, of *Humulus lupulus*, of *Coffea Arabica* and of *Ilex Paraguariensis*.

Extraction from the plant may be performed using conventional engineerings such as phenolic extraction, from any part of the plant such as the flower, seed, fruit, root, tubercle, leaf, pericarp and preferably rhizome. The extraction solvents may be selected from amongst water, propylene glycol, butylene glycol, glycerine, PEG-6 caprylic/capric glycerides, polyethylene glycol, methyl and/or ethyl esters, diglycols, cyclical polyols, ethoxylated or propoxylated diglycols, alcohols (methanol, ethanol, propanol, and butanol) or any mixture of these solvents. Plant extracts according to the present invention may also be obtained by other processes such as maceration, simple decoction, lixiviation, reflux extraction, supercritical extraction with $CO_2$, ultrasound or microwave extraction or counter-current techniques, or by plant cell culture engineerings and/or fermentation. This list is not restrictive.

Suitable peptides can include, but are not limited to, di-, tri-, tetra-, penta-, and hexa-peptides and derivatives thereof In one embodiment, the composition comprises from about $1\times10^{-7}\%$ to about 20%, more preferably from about $1\times10^{-6}\%$ to about 10%, even more preferably from about $1\times10^{-5}\%$ to about 5%, by weight of additional peptide.

As used herein, "peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

Suitable dipeptides for use herein include but are not limited to Carnosine (beta-AH), YR, VW, NF, DF, KT, KC, CK, KP, KK or TT. Suitable tripeptides for use herein include, but are not limited to RKR, HGG, GHK, GKH, GGH, GHG, KFK, GKH, KPK, KMOK, KMO2K or KAvaK. Suitable tetrapeptides for use herein include but are not limited to RSRK (SEQ ID NO:1), GQPR (SEQ ID NO:2) or KTFK (SEQ ID NO:3). Suitable pentapeptides include, but are not limited to KTTKS (SEQ ID NO:4). Suitable hexapeptides include but are not limited to GKTTKS (SEQ ID NO:5), VGVAPG (SEQ ID NO:6) and of the type disclosed in FR 2854897 and US 2004/0120918.

Other suitable peptides for use herein include, but are not limited to lipophilic derivatives of peptides, preferably palmitoyl derivatives, and metal complexes of the aforementioned (e.g., copper complex of the tripeptide His-Gly-Gly). Preferred dipeptide derivatives include N-Palmitoyl-beta-Ala-His, N-Acetyl-Tyr-Arg-hexadecylester (CALMOSENSINE™ from SEDERMA, France, WO 9807744, U.S. Pat. No. 6,372,717). Preferred tripeptide derivatives include N-Palmitoyl-Gly-Lys-His, (Pal-GKH from SEDERMA, France, WO 0040611), Pal-KMO2K, a copper derivative of His-Gly-Gly sold commercially as lamin, from Sigma, lipospondin (N-Elaidoyl-Lys-Phe-Lys) and its analogs of conservative substitution, N-Acetyl-Arg-Lys-Arg-NH2 (Peptide CK+), N-Biot-Gly-His-Lys (N-Biot-GHK from SEDERMA, WO0058347) and derivatives thereof Suitable tetrapeptide derivatives for use herein include, but are not limited to N-palmitoyl-Gly-Gln-Pro-Arg (SEQ ID NO:9) (from SEDERMA, France), suitable pentapeptide derivatives for use herein include, but are not limited to N-Palmitoyl-Lys-Thr-Thr-Lys-Ser (SEQ ID NO:8) (available as MATRIXYL™ from SEDERMA, France, WO 0015188 and U.S. Pat. No. 6,620,419) N-Palmitoyl-Tyr-Gly-Gly-Phe-X with X Met (SEQ ID NO:10) or Leu (SEQ ID NO:11) or mixtures thereof Suitable hexapeptide derivatives for use herein include, but are not limited to N-Palmitoyl-Val-Gly-Val-Ala-Pro-Gly (SEQ ID NO:7) and derivatives thereof.

The preferred compositions commercially available containing a tripeptide or a derivative include Biopeptide-CL™ by SEDERMA (WO0143701), Maxilip™ by SEDERMA (WO 0143701), Biobustyl™ by SEDERMA. The compositions commercially available preferred sources of tetrapeptides include RIGIN™ (WO0043417), EYELISS™ (WO03068141), MATRIXYL™ RELOADED, and MATRIXYL 3000™ which contain between 50 and 500 ppm of palmitoyl-Gly-Gln-Pro-Arg (SEQ ID NO:9), and carrier, proposed by SEDERMA, France (US2004/0132667). The following marketed peptides can be mentioned as well as additional active ingredients: Vialox™, Syn-ake™ or Syn-Coll™ (Pentapharm), Hydroxyprolisilane CN™ (Exsymol), Argireline™, Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), Cytokinol™LS (Laboratoires Serobiologiques/Cognis), Kollaren™, IP2000™ or Meliprene™ (Institut Européen de Biologie Cellulaire), Neutrazen™ (Innovations), ECM-Protect™ (Atrium Innovations), Timp-Peptide™ or ECM Moduline™ (Infinitec Activos), Composition Preparation The compositions of the present invention are generally prepared by conventional methods such as are known in the art of making topical and oral compositions and compositions for injection. Such methods can typically be conducted in one or more steps, with or without heating, cooling, and the like.

The physical form of the compositions according to the invention is not important: they may be in any galenic form such creams, lotions, milk or cream ointments, gels, emulsions, dispersions, solutions, suspensions, cleansers, foundations, anhydrous preparations (sticks, in particular lipbalm, body and bath oils), shower and bath gels, shampoos and scalp treatment lotions, cream or lotion for care of skin or hair, make-up removing lotions or creams, sun-screen lotions, milks or creams, artificial suntan lotions, creams or milks, pre-shave, shave or aftershave creams, foams, gels or lotions, make-up, lipsticks, mascaras or nail varnishes, skin "essences," serums, adhesive or absorbent materials, transdermal patches, or powders, emollient lotion, milk or cream, sprays, oils for the body and the bath, foundation tint bases, pomade, emulsion, colloid, compact or solid suspension, pencil, sprayable or brossable formulation, blush, red, eyeliner, lipliner, lip gloss, facial or body powder, styling foams or gels, nail conditioner, lip balms, skin conditioners, moisturizers, hair sprays, soaps, body exfoliants, astringents, depilatories and permanent waving solutions, antidandruff formulations, anti-sweat and antiperspirant compositions, nose sprays and so on. These compositions can also be presented in the form of lipsticks intended to apply colour or to protect the lips from cracking, or of make-up products for the eyes or tints and tint bases for the face. Compositions in accordance with the invention include cosmetics, personal care products and pharmaceutical preparations. The present invention may also be applied on animal skin and/or appendages. One can also consider a composition in the shape of foam or in the form of compositions for aerosol also including a propellant agent under pressure.

Cosmetic compositions according to the invention may also be for orodental use, for example, toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

The compound according to the present invention may be in the form of solution, dispersion, emulsion, paste, or powder, individually or as a premix or in vehicles individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, spores or exines, micro or nano emulsions or adsorbed on organic polymer powders, talcs, bentonites, or other inorganic or organic supports.

The compound according to the present invention may be used in any form whatsoever, in a form bound to or incorporated in or absorbed in or adsorbed on macro-, micro-, and nanoparticles or macro-, micro-, and nanocapsules, for the treatment of textiles, natural or synthetic fibres, wools, and any materials that may be used for clothing or underwear for day or night intended to come into contact with the skin, handkerchiefs or cloths, to exert their cosmetic effect via this skin/textile contact and to permit continuous topical delivery.

Method of Topical Cosmetic or Dermopharmaceutical Treatment

The present invention also concerns a topical treatment process to improve the general condition of the skin involving topical application to the skin of an effective amount of the composition of the invention as recited above. More specifically:

to prevent and/or treat the signs of intrinsic and extrinsic skin ageing;

to prevent and/or treat skin dehydration;

to prevent and/or treat skin sagging and/or improve tone and/or firmness and/or elasticity and/suppleness of the skin;

to prevent and/or treat skin atrophy and/or improve the density of the dermis and epidermis;

to give or return volume to the dermis and epidermis;

for stimulating the expansion of adipose tissue.

to lighten the skin;

to prevent and/or treat skin roughness;

to prevent and/or treat degradation of the skin due to the effects of oxidation;

to prevent and/or treat hair loss;

to prevent and/or treat glycation of molecules in the skin;

to prevent and/or treat acne;

to prevent and/or treat inflammatory states.

The composition according to the invention may be applied locally onto areas of the face, lips, neck, neckline, hands, feet, head or body. One of the major advantages of the present invention resides in the ability whenever necessary or desirable to be able to apply local selective "gentle" treatments through this topical, non-invasive method of application. In the case of anti-wrinkle use for example it may be applied very locally using a syringe or micro-canula.

It is also possible, however, to consider a composition containing the compound according to the invention intended to be injected subcutaneously.

According to other specific features the treatment method according to the invention can be combined with one or more other treatment methods targeting the skin such as luminotherapy, aromatherapy or heat treatments.

According to the invention, devices with several compartments or kits may be proposed to apply the method described above which may include for example and non-restrictively, a first compartment containing a composition including the invention lipo-sulphated or lipo-phosphated compound, and in a second compartment a composition containing another active ingredient and/or excipient, the compositions contained in the said first and second compartments in this case being considered to be a combination composition for simultaneous, separate or stepwise use in time, particularly in one of the treatment methods recited above.

EXAMPLES

The following examples describe and demonstrate various aspects within the scope of the present invention. The examples are only given for illustrative purposes and should not be considered to be restrictive to this invention. Additionally for illustrative purposes several cosmetic formulations will be described. These formulations are representative of but do not restrict the invention.

1/Example of Manufacture Method for Obtaining the Lipo-Phosphomalate (Ester 4-tetradecyle of the 2-phosphate-succinic acid) According to the Invention The synthesis of the 2-phosphate-succinic acid 4-tetradecyl ester (final product with the 2 reference) is realized in 4 linear steps according to the following synthesis schema:

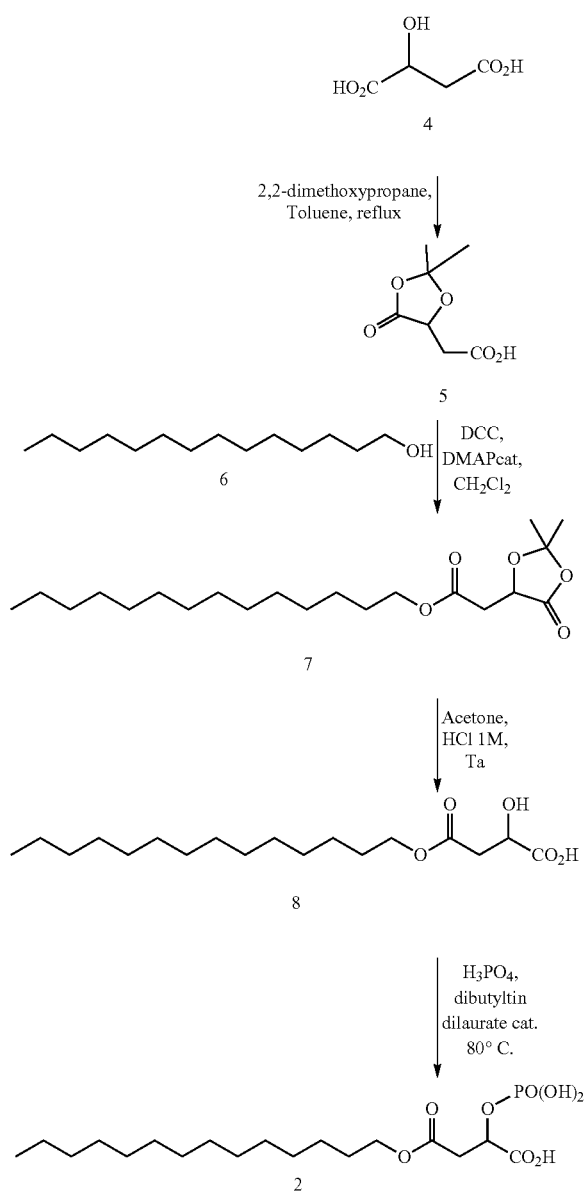

Synthesis of the (2,2-dimethyl-5-oxo-[1,3]dioxolan-4-yl)-acetic acid (With the 5 Reference on the Above Schema)

Marketed DL-malic acid (with the 4 reference on the above schema) is protected in the dioxolane form in toluene reflux, in the presence of 2,2-dimethoxypropane. The reaction is quantitative. The obtained product (with the 5 reference in the above schema) is directly engaged in the following step.

Synthesis of (2,2-Dimethyl-5-oxo-[1,3]dioxolan-4-yl)-acetic acid tetradecyl ester (With the 7 Reference in the Above Schema)

The free carboxylic function is esterified with 1-tetradecanol, in the presence of DCC (Dicyclohexylcarbodiimide) and of a catalytic amount of DMAP3 (4-dimethylaminopyridine). The obtained compound (with the 7 reference in the above schema) is directly engaged in the following step.

Synthesis of the Succinic acid 4-tetradecyl ester (With the 8 Reference in the Above Schema)

The cetal (ref 7) is hydrolyzed in an acid medium to conduct to the acid. The isolated product yield is of 71% after purification and cristallisation in cyclohexane.

Synthesis of the 2-Phosphate-succinic acid 4-tetradecyl ester (Ref 2)

The free alcohol function is phosphated with phosphoric acid in the presence of a catalytic amount of dibutyltin dilaurate, at 80° C. The desired lipo-phospho-malate (ref 2) is obtained with a 46% yield in the form of a white solid.

2/Formulation Example of an Active Ingredient Comprising the Invention Compound

This active ingredient is for the cosmetic industry for the preparation of cosmetic products, such as creams, gels, etc.

The solid Lipo-Phosphomalate is first solubized in a mixture of sugar esters (laurate and/or oleate sorbitan) and of phosphated esters (oleyl and/or dioleyl phosphates), then dispersed in an emollient. Typically, the amount of Lipo-Phosphomalate in this active ingredient will be of about 200 ppm.

3/In Vitro Evaluation Results

For theses evaluation tests, when the Lipo-Phosphomalate is solubilized, it is according to the above point 2/.

Filaggrin is a protein found in the upper part of the epidermis. It is a key factor in water homeostasis by virtue of its crucial role in forming and then stabilizing the cutaneous barrier (stratum corneum), and in crating the Natural Moisterising Factor (NMF).

Filaggrin is produced by the granular layer—the last viable of the epidermis—in the form of a polymeric precursor: the profilaggrin. The latter is a chain of 1 to 12 filaggrin monomers. Its phosphorylation rate controls its insolubility, lysis and packing in kertohyalin granules with loricrine and keratins 1 and 10.

Successively and, as it will rise towards the upper layers of the epidermis, profilaggrin will undergo:
- a proteolysis leading to the production of monomers of filaggrin. Matriptase is involved in this proteolysis;
- a binding on the keratin intermediate filaments (KIF) thanks to TGase;
- the de-imination of filaggrin by a peptidyl deiminase to reduce the binding and leading to the reappearance of filaggrin monomers, and
- the degradation of filaggrin into filaggrin fragments by an unidentified protease.

In the lower part of the stratum corneum, dehydration triggers the complete proteolysis of filaggrin fragments under the action of caspase-14. This proteolysis leads to the production of hygroscopic amino acids. These amino acids form about 40% of the natural moisturizing factor (NMF), partly responsible for the maintenance of good hydration of the epidermis.

Good hydration of the epidermis is a complex phenomenon involving maintaining a high level of expression of different proteins: filaggrin, TGase, loricrine, matriptase and caspase 14. This is achieved through the application on human keratinocytes in culture or on skin explants.

Proper hydration of the skin is also ensured by the presence at the horny layer of a particularly impermeable lipid membrane, which prevents water loss.

3.1—Study of Filaggrin Synthesis on Human Keratinocytes (Immunofluorescent Method)

Protocol: Human keratinocytes were cultivated up to confluence. The cells were then placed in contact/not contact with the solubilized Lipo-Phosphomalate for 21 days. At the end of this contact period, labelling common to both filaggrin and profilaggrin was carried out on cell layers using specific antibodies. Labelling intensity was analysed on photos (n=15 photos) and compared to that obtained for the negative control and for vitamin D3 at $10^{-7}$M used as a positive differentiation control.

TABLE 1

Production of filaggrine and profilaggrin in human keratinocytes in the presence of solubilised Lipo-Phosphomalate

|  | Concentration | Filaggrin/profilaggrin (UFA/$10^6$ cell.) | Change (%); significance |
|---|---|---|---|
| Control | — | 1.39 ± 0.62 | Reference |
| Solubilised Lipo-Phosphomalate | 1.5 ppm | 3.04 ± 1.21 | +119%; p < 0.01 |
|  | 5 ppm | 5.00 ± 1.58 | +259%; p < 0.01 |

Vitamin D3 ($10^{-7}$ M): +221% (p < 0.01)

The positive control used strongly induced profilaggrin and filaggrin synthesis in cells. At the same time, increasing concentrations of the solubilised Lipo-Phosphomalate stimulated this production in a dose-dependent manner. An increase of +259% (p<0.01) was recorded in the presence of 5 ppm of solubilised Lipo-Phosphomalate compared to control.

3.2—Highlighting of the Increase of Filaggrin/Profilaggrin Synthesis in Explanted Human Skin in the Presence of Solubilised Lipo-Phosphomalate The filaggrin/profilaggrin synthesis has been confirmed in explanted human skins. This model, highly realistic, corroborates the results obtained on single layer cultures.

Experimental Protocol:

The day after their preparation (removal from adipose tissue), a cream containing 5 ppm of solubilised Lipo-Phosphomalate was topically applied to skin segments measuring 8 mm in diameter, every day for 5 days (cream prepared with the active ingredient of point above 2/) (n=3 skin segments). At the same time the placebo cream was applied to control skins (n=3). Following applications, the skin segments were fixed, frozen and then cut using a cryomicrotome. The slides obtained were labelled with the same antibody as before. The fluorescent filaggrin/profilaggrin markers obtained for the cream with the Lipo-Phosphomalate were quantified by image analysis (n=30 photos for each case) and compared to those obtained with the placebo cream.

In a second series of experiments, the skin segments were lightly stripped in advance (4 successive strips), in order to improve the active penetration, and then are subjected to the same procedure as before.

Results:

The photos show the variation in the quantity of filaggrin/profilaggrin in the upper section of the human skin epidermis following application of the cream containing the solubilised Lipo-Phosphomalate or the placebo cream.

TABLE 2

Production of filaggrin and profilaggrin induced by the Lipo-Phosphomalate by human skin

|  |  | Filaggrin/profilaggrin (UFA) | Change (%); significance |
|---|---|---|---|
| Intact skins | Placebo cream | 8.59 ± 2.00 | Reference |
|  | Cream with 5 ppm of solubilised Lipo-Phosphomalate | 11.40 ± 2.90 | +33%; p < 0.01 |
| Stripped skins | Placebo cream | 8.55 ± 1.70 | Reference |
|  | Cream with 5 ppm of solubilised Lipo-Phosphomalate | 14.43 ± 3.10 | +69%; p < 0.01 |

A marked increase in the filagrin fluorescent signal was observed in the skins that had received the cream at 5 ppm of solubilised Lipo-Phosphomalate compared to the skins that had received the placebo cream.

Similarly, the results of the analysis recorded for the stripped skin show that the cream containing 5 ppm of solubilised Lipo-Phosphomalate stimulates filaggrin/profilaggrin production to a highly significant extent compared to the control. It is interesting to note that the same quantity of filaggrin was obtained with the placebo, regardless of whether or not the strips were used. The stripping before compound application therefore improved the efficacy of the solubilised Lipo-Phosphomalate facilitating its penetration.

These two studies, together with the one realised on the cultured keratinocytes, show that the solubilised Lipo-Phosphomalate can increase the quantities of filaggrin/profilaggrin in the epidermis.

3.3—Study of the Synthesis of Caspase-14 and Matriptase

These two enzymes are responsible of the metabolism of pro-filaggrin and filaggrin.

The method disclosed in example 1.2- was used.

Results

TABLE 3

Production of matriptase and caspase-14 in the presence of solubilised Lipo-Phosphomalate in cultured human keratinocytes by immunolabelling (n = 15 photos)

|  | Concentrations | Matriptase (UFA/$10^6$ cell.) | Change (%); significance | Caspase (UFA/$10^6$ cell.) | Change (%); significance |
|---|---|---|---|---|---|
| Control | — | 1.01 ± 0.34 | Reference | 0.51 ± 0.16 | Reference |
| Solubilised Lipo-Phosphomalate | 1.5 ppm | 2.27 ± 0.47 | +125%; p < 0.01 | 1.13 ± 0.44 | +121%; p < 0.01 |
|  | 5 ppm | 4.08 ± 1.56 | +304%; p < 0.01 | 1.68 ± 0.64 | +229%; p < 0.01 |

Vitamin D3 ($10^{-7}$ M): +239% and +571% (p < 0.01)

The results show that the matriptase increases in a similar pattern to filaggrin in the layers of keratinocytes. Induction was significant and dose-dependent on the quantity of solubilised Lipo-Phosphomalate to reach +304% at 5 ppm.

Induction of caspase-14 synthesis (+229%; p<0.01) was also noted with 5 ppm of solubilised Lipo-Phosphomalate. As for the matriptase, a parallelism with the increase of filaggrin synthesis is noted.

It appears therefore that filaggrin formation is not the only phenomenon to be promoted by the solubilised Lipo-Phosphomalate, but that the enzymes, which produce the wetting component on cleaving filaggrin, are also stimulated, and in similar proportions.

3.4—Study of the Synthesis of Loricrine

Loricrine is one of the key elements in the formation of the corneal envelope. It is attached to involucrin (see 1.1) by transglutaminase, which forms rigid, insoluble structures. The method described in 1.2. was used.

TABLE 4

Production of loricrin in the presence of solubilised Lipo-Phosphomalate in cultured human keratinocytes by immunolabelling (n = 15 photos)

| | Concentrations | Loricrin (UFA/10$^6$ cell.) | Change (%); significance |
|---|---|---|---|
| Control | — | 0.73 ± 0.48 | Reference |
| Solubilised Lipo-Phosphomalate | 1.5 ppm | 1.69 ± 0.67 | +131%; p < 0.01 |
| | 5 ppm | 3.84 ± 1.19 | +426%; p < 0.01 |

Vitamin D3 (10$^{-7}$ M): +206% (p < 0.01)

As for the three preceeding proteins, a highly stimulation of the synthesis of loricrin by the solubilised Lipo-Phosphomalate is also observed.

3.5—Study of the Transcription and Activity of Transglutaminase

Transglutaminase was studied using the transcription by m-RNA, qRT-PCR and regarding activity by enzymological assay.

ByqRT-PCR: Human keratinocytes were placed in contact/not placed in contact with solubilised for 14 days. At the end of the contact period, the cultures were stopped and m-RNA allowing production of transglutaminase-1 protein was quantified using the RT-PCR method.

After extraction and purification of the m-RNA, copies are made in DNA using a Reverse Transcriptase (RT). The number of copies of a given m-RNA (here that of TGase) is thereafter amplified using two oligonucleotides (called primers) specific to the gene of TGase and to an enzyme (PCR=polymerase chain reaction) during a series of amplification cycles, each of which doubling the number of copies present. The result of this amplication is measured by fluorescence. Ct is the number of cycles required to achieve a given fluorescence level (arbitrarily set). It is clear, that the more m-RNA of a given gene present in the starting culture there are, the fewer cycles (Ct) are needed to reach the set level of fluorescence.

By Enzymology:

At the end of the 14-day contact period, the cells were placed in contact with a fluorescent synthetic transglutaminase substrate. Metabolisation of the substrate via transglutaminase will allow the fixation in the intracellular protein matrix. After rinsing, the non fixed fluorescent substrate is eliminated and the fluorescence fixed in the cells by the enzyme is quantified.

TABLE 5

Production of transglutaminase-1 m-RNA and of the variation of transglutaminase activity in the presence of solubilised Lipo-Phosphomalate in the keratinocytes (n = 5)

| | | m-RNA | | Enzymology | |
|---|---|---|---|---|---|
| | Concentrations | Number of cycles: Ct* | % change**; Significance | Transglutaminase (UFA/10$^6$ cell.) | % Change; Significance |
| Control | — | 24.60 ± 0.42 | Reference | 230 ± 43 | Reference |
| Solubilised Lipo-Phosphomalate | 5 ppm | 23.25 ± 0.46 | +101%; p < 0.01 | 516 ± 63 | +124%; p < 0.01 |

Vitamin D3 (10$^{-7}$ M): m-RNA⇔ +73% and Enzymology⇔ ×7.5 (p < 0.01)
*One Ct unit corresponds to approximately 100% variation.
**After normalisation by the «housekeeping» gene, invariable in concentration, with or without solubilised Lipo-Phosphomalate.

These results show that transglutaminase is induced by the solubilised Lipo-Phosphomalate, both at transcriptional level (m-RNA) and at the protein activity level. In both cases, the increase is close to +100% (p<0.01).

In addition, a DNA-Array study has shown that the transglutaminase-1 and involucrin genes are over-expressed in the network with other genes essential for the formation of the corinfied layer in the presence of solubilised Lipo-Phosphomalate.

Induction of TGase synthesis by the solubilised Lipo-Phosphomalate completes this picture of the stimulation of the protein essential to form the skin barrier. What is remarkable in the invention is the simultaneous stimulation in the presence of solubilised Lipo-Phosphomalate of these five proteins, each essential for hydration.

3.6—Evaluation of the Effect of the Lipo-Phosphomalate on Complex Lipids Synthesis The skin is made up of several layers of cells protecting us from external agressions by various means. The main mean among them is a lipid barrier in the stratum corneum, the outermost layer of skin, consisting mainly of ceramides, cholesterol and fatty acids allowing the skin to retain its hydration. We studied the effect of Lipo-Phosphomalate on the synthesis of cholesterol and ceramides in cultured human keratinocytes.

Cholesterol (Immunolabelling)

Cultured human keratinocytes at confluence were placed in contact with the Lipo-Phosphomalate in a medium slightly enriched with calcium to promote the establishment of intercellular junctions and thus improve the anchorage of differentiated cells to the underlying cells. A negative control was carried out in the same medium. After a 7-day contact period, the layer was labeled with a cholesterol-specific fluorescent.

The intensity of the labeling was analysed on the photos and compared to that obtained with the negative control (Table 6).

Photos of the Lipo-Phosphomalate cases show the onset of marked differentiation visible beneath the microscope. The cells are linked in large cohesive bundles, sometimes interlinked as though via a network. This was not observed with the negative control over the same period.

In addition to quantification by immunological labeling, cholesterol quantification was carried out using high-performance thin-layer chromatography (or HPTLC).

Cholesterol (Thin-Layer Chromatography)

The same protocol was followed as before but a larger quantity of keratinocyes was used on this occasion because of the limits of detection of the apparatus. After 7 days, the layers were rinsed, lipids extracted using solvents before being deposited on a thin-layer chromatography plate using an automated device. After migration and detection, the bands were analysed and quantified based on a range of standard lipids deposited on the same plate.

terms of both the production of corneocyte gorged with a crosslinked protein matrix and the production of its essential lipids. Filaggrine, caspase-14 and matriptase form the basiss of the production of water homiostatis; involucrin, loricrine and transglutaminase are the key elements of the corneocyte formation; ceramides and cholesterol complete this picture for the formation of the hydro-lipid barrier.

3.7—Synthesis of Hyaluronic Acid and its Receptor CD44

The cited main interest of hyaluronic acid is its role as a moisturizer agent for the skin epidermis and also as anti-wrinkle agent, because participating to the elasticity of the skin. Hyaluronic acid is present in the intercellular spaces of the basal and spineous layers, mainly of the medium spineous layer, but absent from the upper layers (granular and horny). Its hydration role is therefore positioned at the lower layers of the epidermis, unlike the previously mentioned effects that were located in the upper layers of the epidermis.

TABLE 6

Variation of the quantity of cholesterol by immunolabelling and HPTLC in keratinocytes after contact with solubilised Lipo-Phosphomalate

| | | IMF | | HPTLC | |
|---|---|---|---|---|---|
| | Concentrations | Cholesterol $(UFA/10^6 cell.)$ | % Change*; Significance | Cholesterol $(pg/10^6 cell.)$ | % Change; Significance |
| Control | — | 2.40 ± 2.37 | Reference | 20.24 ± 2.40 | Reference |
| Solulbilised Lipo-Phosphomalate | 5 ppm | 4.98 ± 2.59 | +107%; $p < 0.04$ | 30.89 ± 7.20 | +53%; $p < 0.05$ |

These two results, obtained with two different methods, show that the Lipo-Phosphomalate stimulate the production of cholesterol during keratinocyte differenciation.

Ceramides

At the same time as the HPTLC cholesterol assay, an assay of hydroxylated and non-hydroxylated ceramides was carried out on the extracts.

Effect on the Synthesis of Hyaluronic Acid by Human Keratinocytes Humains

Protocol: Human keratinocytes are humains were cultivated in MW24 plates for 24 h. Cells were contacted or not with the Lipo-Phosphomalate for 3 days. Culture surpernatants were taken and an assay of the quantity of hyaluronic acid was achieved. Retinoic acid was used as the positive control.

TABLE 7

Variation of the quantity of ceramides by HPTLC in the keratinocytes after contact with the solubilised Lipo-Phosphomalate

| | Concentrations | Non hydroxylated Ceramides $(pg/10^6 cell.)$ | % Change*; Significance | Hydroxylated Ceramides $(pg/10^5 cell.)$ | Change*; Significance |
|---|---|---|---|---|---|
| Control | — | 2.36 ± 0.10 | Reference | 1.40 ± 0.01 | Reference |
| Solubilised Lipo-Phosphomalate | 5 ppm | 8.41 ± 1.30 | +256%; $p < 0.01$ | 10.50 ± 1.12 | ×7.5 |

*number of times.

These data clearly show that the Lipo-Phosphomalate induces the production of chorlesterol and of various classes of ceramides in keratinocytes during their differentiation. This lipid production by the Lipo-Phosphomalate was not observed in fibroblasts or melanocytes. It is therefore a specific effect related to the metabolism of keratinocyte during its differentiation.

All this information clearly shows that the Lipo-Phosphomalate triggers in cultured human keratinocytes the production of the elements essential for the introduction and homeostasis of hydration and skin barrier. Thus a number of syntheses converge to create the cornified cell envelope in

TABLE 8

Increase of the hyaluronic acid by the Lipo-Phosphomalate on human keratinocytes (ELISA) (n = 5)

| | Concentration | $ng/10^e6$ cells | % Change/control |
|---|---|---|---|
| Control | — | 878 +/− 21 | Reference |
| Solubilised Lipo-Phosphomalate | 1.67 ppm | 1015 +/− 46 | +16%; $p < 0.01$ |
| | 5 ppm | 1374 +/− 50 | +57%; $p < 0.01$ |
| | 8.33 ppm | 1480 +/− 51 | +69%; $p < 0.01$ |

Retinoic acid (positive control) 1 μM = +190%; $p < 0.01$.

A dose-dependent and significant stimulation of the synthesis of hyaluronic acid in the human keratinocyte in the presence of the Lipo-Phosphomalate of the invention is observed.

Effect of the CD44 Synthesis for the Keratinocyte

Protocol:

Human keratinocytes were cultivitated in 35 mm box to confluence. Cells are contacted or not with the Lipo-Phosphomalate for 22 days. At the end of this contact period, the cells are fixed and an immunological labeling of the CD44 is made using specific antibodies.

TABLE 9

Increase of the CD44 synthesis in the presence of the Lipo-Phosphomalate by human keratinocytes

| | Concentration | UFA/$10^6$ cells | % Variation/control |
|---|---|---|---|
| Control | — | 3.96 +/− 3.65 | Reference |
| Solubilized Lipo-Phosphomalate | 5 ppm | 27.20 +/− 16.5 | +587%; p < 0.01 => ×7 |

A dose dependent and significant stimulation of the keratinocyte CD44 in the presence of the Lipo-Phosphomalate of the invention is observed.

3.8—Effect on the Laminin Synthesis by Human Keratinocytes

The laminin molecule is important at the level of the dermo-epidermal junction (DEJ). It ensures proper anchoring of basal keratinocytes to the basement membrane and is responsible for the suppleness of the epidermis. In aged cells it is no longer replaced as efficiently as in young cells, hence the need to stimulate the biosynthesis for an improved renewal.

Protocol:

Human keratinocytes are humains were cultivated in MW24 plates for 24 h. Cells were contacted or not with the Lipo-Phosphomalate for 3 days. Culture surpernatants were taken and an assay of the quantity of laminin was achieved. TGF-β1 was used as the positive control.

TABLE 10A

Increase of the laminin by the Lipo-Phosphomalate on human keratinocytes (ELISA) (n = 5)

| | Concentration | ng/$10^6$cells | % Variation/control |
|---|---|---|---|
| Control | — | 116 +/−13 | Reference |
| Solubilized Lipo-Phosphomalate | 1.67 ppm | 190 +/− 11 | +64%; p < 0.01 |
| | 5 ppm | 333 +/− 10 | +187%; p < 0.01 |
| | 8.33 ppm | 343 +/− 10 | +196%; p < 0.01 |

TGF-β1 (positive control) $10^{-6}$% = +361%; p < 0.01

A dose dependent and significant stimulation of the laminin synthesis in the keratinocyte in the presence of the Lipo-Phosphomalate of the invention is observed.

This makes the Lipo-Phosphomalate of the invention particularly well suited for anti-aging, in particular for anti-wrinkles and firming applications.

3.9—Synthesis of Collagen I on Human Dermal Fibroblast

Normal human fibroblasts (NHF) are cultivated in MW24 plates for 24 hours. The cells are contacted or not with the Lipo-Phosphomalate of the invention at various concentrations for 7 days. The synthesis of collagen I produced by the cells is then quantified by immunolabeling fixed on the layers using a specific antibody. Quantification by image analysis is then performed on the photos. TGF-β1 is used as positive control.

An analysis of variance was performed on the data (cases treated compared with untreated cases). In the case of identity of variances, a Student't test was then performed on the means.

Results:

TABLE 10B

Increased synthesis of collagen I in the fibroblast (n = 15 files/cases)

| | Concentration | AFU mean | % Variation/control |
|---|---|---|---|
| Contrôle | — | 3.7 +/− 2.1 | Reference |
| Solubilized Lipo-Phosphomalate | Eq 1% | 8.1 +/− 5.6 | +60%; p = 0.09 |
| | Eq 3% | 21.1 +/− 13.8 | +315%; p < 0.01 |
| | Eq 5% | 30.4 +/− 14.6 | +496%; p < 0.01 |
| TGF-β1 | $10^{-6}$% | 55 +/− 17.6 | +1374%; p < 0.01 |

AFU=arbitrary fluorescen unit

A dose-dependent and significant stimulation of the synthesis of collagen I in the dermal fibroblasts in the presence of Lipo-Phosphomalate according to the invention is observed.

This makes the Lipo-Phosphomalate of the invention particularly well suited for preventing and repairing skin damages, comprising loss of the mechanical properties of the skin (loss of firmness), fine lines and wrinkles.

3.10—Study of the Lipo-Phosphomalate on Adipogenesis

Some cosmetic compounds are designed to encourage the installation of the subcutaneous fat for better aesthetics and greater volume. In this perspective, increase adipocyte differentiation was considered in in vitro tests, (with the key marker G3PDH) on pre-adipocyte cultures and, similarly, lipogenesis stimulation in these cultures was considered.

Effect of the Lipo-Phosphomalate on G3PDH Activity

Protocol:

3T3-L1 cells were cultivated until sub-confluence, then induced to differentiate with the appropriate mixture with or without the Lipo-Phosphomalate at different concentrations. After 3 days of incubation, the differenciation mixture is replaced by a new maintaining culture medium, in the presence or not of the Lipo-Phosphomalate. After 3 days of incubation, the cell layers are collected and the activity of G3PDH is assayed.

TABLE 11

| | Concentration | % Change/control |
|---|---|---|
| Control | — | Reference |
| Lipo-Phosphomalate | 10 ppm | +158%; p < 0.01 |
| | 15 ppm | +225%; p < 0.01 |

Pioglytazone (positive control) 10 μM: +593%; p < 0.01

The results show that the differenciation of the pre-adipocytes is dose dependent and significantly stimulated by the Lipo-Phosphomalate.

Effect of the Lipo-Phosphomalate on the Synthesis of Triglycerides

Protocol:

3T3-L1 cells were cultivated until sub-confluence, then induced to differentiate with the appropriate mixture with or without the Lipo-Phosphomalate at different concentrations. After 3 days of incubation, the differenciation mixture is replaced by a new maintaining culture medium, in the presence or not of the Lipo-Phosphomalate. After 3 days of incubation, the quantity of intracellular triglycerides is measured by enzymatic method.

TABLE 12

|  | Concentration | % Change/control |
|---|---|---|
| Control | — | Reference |
| Lipo-Phosphomalate | 10 ppm | +112%; p < 0.01 |
|  | 15 ppm | +210%; p < 0.01 |

Pioglytazone (positive control) 10 μM: +174%; p < 0.01

Stimulation of the Lipid Incorporation by the 3T3-L1 Cells
Protocol:

3T3-L1 cells are sowed and cultivated for 4 days (multiplication). Follow a differentiation phase (incubation with a classic differentiation mixture) and then a maturation phase (with a maturation mixture) in the presence or not of the Lipo-Phosphomalate at different concentrations. At the end of this period, cells were washed, fixed and coloured with oil red. The cell layers were photographed digitally and the red color is quantified by image analysis. The surface percentages of red oil, reported in the table below, were established compared to untreated control cells, and the test validated by comparison to pioglytazone (10 μM), positive control for stimulation of differentiation.

TABLE 13

|  | Concentration | % Change/control |
|---|---|---|
| Control | — | Reference |
| Lipo-Phosphomalate | 10 ppm | +171%; p < 0.01 |
|  | 15 ppm | +294%; p < 0.01 |
|  | 20 ppm | +481%; p < 0.01 |

Pioglytazone (positive control) 10 μM: +323%; p < 0.01

The results show that the Lipo-Phosphomalate is dose dependently stimulating the differentiation and sysnthesis of triglycerides on pre-adipocytes. The Lipo-Phosphomalate can promote body volume by a cosmetic lipofilling-like effect.

3.11—Melanogenesis Study
Protocol:

Human melanocyte are sowed and contacted with the Lipo-Phosphomalonate for 5 days. At the end of the incubation period, the residual tyrosinase activity was measured in cell homogenates.

TABLE 14

Change in the tyrosinase activity of human melanocytes after 5 days of contact with the Lipo-Phosphomalonate

|  | Concentration | Variation (%) |
|---|---|---|
| Control | — | Reference |
| Lipo-Phosphomalate | 10 ppm | −21%; p < 0.01 |
|  | 12 ppm | −28%; p < 0.01 |
|  | 15 ppm | −31%; p < 0.01 |

Arbutin (positive control) 0.03% = −45%; p < 0.01

A significant and dose-dependent decrease of the tyrosinase activity is observed in the presence of the Lipo-Phosphomalate.

The Lipo-Phosphomalate of the invention is therefore useful for lightening the skin All these results show that the Lipo-Phosphomalate of the present invention is an agent able to act on different levels: hydration, mechanical properties (firmness, suppleness), fines lines and wrinkles, give or return volume of the dermis, depigmentation of age spots . . . . The compound of the invention can be preconized for one these properties or as a global anti-ageing agent.

4/Galenic

The active ingredient described in point 1/ above (containing about 200 ppm of the Lipo-Phosphomalate) is used below to formulate cosmetic products.

4.1/Hydration Gel

| Product | % | CTFA name |
|---|---|---|
| Phase A |  |  |
| H$_2$O | Qsp100 | Water |
| Ultrez 10 Carbopol | 0.20 | Carbomer |
| Phase B |  |  |
| Butylene glycol | 2.00 | Butylene glycol |
| Preservative | qs |  |
| Phase C |  |  |
| Cithrol GMS A/S NA | 1.00 | Glyceryl stearate & PEG 100 stearate |
| Crodacol CS 90 | 0.50 | Cetearyl Alcohol |
| Crodamol AB | 2.00 | C12-15 Alkyl Benzoate |
| Crodamol OSU | 3.00 | Dioctyl succinate |
| Phase D |  |  |
| Pemulen TR2 | 0.20 | Acrylates/C10-30 Alkyl Acrylates cross polymer |
| Crodamol STS | 1.00 | PPG-3 Benzyl Ether Myristate |
| DC 245 | 1.00 | Cyclopentasiloxane |
| Phase E |  |  |
| Potassium sorbate | 0.10 | Potassium Sorbate |
| Phase F |  |  |
| Active ingredient comprising 200 ppm of Lipo-Phosphomalate of the invention | 3.00 |  |
| Phase G |  |  |
| H$_2$O | 4.00 |  |
| NaOH 30% | 0.40 | Sodium Hydroxide |

Operating Procedure:

Stage 1: Weigh phase A and allow it to swell without stirring for 30 min
Stage 2: Weigh phase B and mix thoroughly.
Stage 3: Then add phase B into phase A, mix thoroughly.
Stage 4: Heat phase A+B at 75° C. in a water bath.
Stage 5: Weigh phase C and heat at 75° C. in a water bath. Mix thoroughly.
Stage 6: Weigh phase D and mix thoroughly.
Stage 7: Add phase C, then phase D in phase A+B with stirring staro v=1000 rpm, homogenise well.
Stage 8: extemporaneously, add phase E, pre-warmed to 60° C.
Stage 9: Then add phase F, homogenise thoroughly.
Stage 10: Around 55° C. add Phase G, homogenise thoroughly.

4.2/Hydration Cream

| Product | % | CTFA name |
|---|---|---|
| Phase A |  |  |
| H$_2$O | qsp100 | Water |
| Ultrez 10 | 0.25 | Carbomer |
| Phase B |  |  |
| Butylene glycol | 2.00 | Butylene glycol |
| Phenoxyethanol | qs | Phenoxyethanol |

-continued

| Product | % | CTFA name |
|---|---|---|
| Phase C | | |
| Volpo S2 | 0.40 | Steareth-2 |
| Volpo S 10 | 1.20 | Steareth-10 |
| Cithrol GMS AS/NA | 1.00 | Glyceryl stearate & PEG-100 stearate |
| Crodacol CS90 | 0.50 | Cetearyl Alcohol |
| Laurocapram | 2.50 | Azone |
| DC 345 | 2.00 | Cyclohexasiloxane & Cyclopentasiloxane |
| Crodamol OSU | 7.00 | Dioctyl Succinate |
| Phase D | | |
| Active ingredient comprising 200 ppm of Lipo-Phosphomalate of the invention | 3.00 | |
| Phase E | | |
| Potassium sorbate | 0.10 | Potassium Sorbate |
| Phase F | | |
| H₂O | 3.00 | Water |
| NaOH 30% | 0.25 | Sodium Hydroxide |

Operating Procedure:

Stage 1: Weigh phase A and allow it to swell without stirring for 30 min

Stage 2: Heat phase A at 75° C. in a water bath.

Stage 3: Weigh phase B and mix thoroughly.

Stage 4: Then add phase B in phase A at 75° C. in a water bath.

Stage 5: Weigh phase C and heat at 75° C. in a water bath. Mix thoroughly.

Stage 6: Add phase C in phase A+B with stirring staro v=1000 rpm, homogenise thoroughly.

Stage 7: extemporaneously, add phase D, pre-warmed to 60° C.

Stage 8: Then add phase E, homogenise thoroughly.

Stage 9: Adjust the pH to 6 with phase E below 350 C.

Stage 10: Then add phase F, homogenise thoroughly.

4.3/Hydration/anti-ageing cream: a combination of the Lipo-Phosphomalate compound according to the invention, in particular for its hydration properties, and of the Essenskin® active marketed by the Applicant for its anti-ageing properties. Essenskin® will consolidate the anti-ageing properties of the compound of the present invention.

Essenskin® is an association of calcium α-hydroxymethionine and homotaurine.

| Product | % | CTFA name |
|---|---|---|
| Phase A | | |
| H₂O | qsp100 | Water |
| Optasens G 83 | 0.30 | Carbomer |
| Phase B | | |
| Arlatone LC | 4.00 | Sorbitan stearate & sorbityl laurate |
| Phase C | | |
| Glycerin | 5.00 | Glycerin |
| Phenoxyethanol | qs | Phenoxyethanol |
| Phase D | | |
| Crodacol CS 50 | 0.50 | Cetearyl alcohol |
| Estol 3609 | 3.00 | Triethylhexanoin |

-continued

| Product | % | CTFA name |
|---|---|---|
| Prisorine 2021 | 3.00 | Isopropyl Isostearate |
| Dow Corning 345 | 2.00 | Cyclohexasiloxane & cyclopentasiloxane |
| Phase E | | |
| Active ingredient comprising 200 ppm of Lipo-Phosphomalate of the invention | 3.00 | |
| Phase F | | |
| Potassium sorbate | 0.10 | Potassium Sorbate |
| Phase G | | |
| H₂O | 3.00 | Water |
| NaOH 30% | 0.25 | Sodium hydroxide |
| Phase H | | |
| Essenskin® | 2.50 | |
| Phase I | | |
| Verveine fragrance | 0.10 | Fragrance |

Operating Procedure:

Stage 1: Sprinkle Ultrez 10 in water and allow it to swell for 30 min

Stage 2: Heat phase A at 75° C. in a water bath.

Stage 3: Weigh phase B and mix thoroughly. Sprinkle phase B in phase A, in a water bath at 75° C., with stirring v=300 rpm. Allow it to homogenize 30 minutes.

Stage 4: Weigh and mix phase C. Add phase C in phase A+B in a water bath at 75° C.

Stage 5: Weigh phase D and heat at 75° C. in a water bath.

Stage 6: Add phase E in phase D.

Stage 7: Poor phase D+E in phase A+B+C, with stirring v=1000 rpm, outside the waterbath.

Stage 8: Extemporaneously add phase F.

Stage 9: Slowling neutralise with phase G by adjusting the pH, allow it to swell for 1 hour.

Stage 10: Below 35° C., check the pH=+1-6.00.

Stage 11: Add phase H in the preceeding phase, mix thoroughly.

Stage 12: Add phase I in the preceeding phase, mix thoroughly.

4.4/Firming/Hydration Anti-Ageing Cream:

a combination of the compound of the invention, in particular for its hydration properties and of the Idealift® active marketed by the Applicant for its firming/anti-sagging properties.

Idealift® contains the lipodipeptide N-acetyl-Tyrosyl-Arginyl-O-hexadecyl ester. It is an active able to stimulate the synthesis of elastic fibers and has an anti-gravity effect on the face skin. The lipopeptide is also known for its calming and myorelaxing properties.

| Product | % | CTFA name |
|---|---|---|
| Phase A | | |
| Optasens G83 | 0.30 | Carbomer |
| H₂O | qsp100 | Water |
| Phase B | | |
| Phenoxyethanol | qs | Phenoxyethanol |
| Glycerin | 3.50 | Glycerin |

-continued

| Product | % | CTFA name |
|---|---|---|
| Phase C | | |
| Optasens G82 | 0.20 | Acrylic acid/Alkyl-methacrylate copolymer |
| Polawax GP 200 | 1.00 | Cetearyl alcohol & polysorbate 20 |
| Crodacol CS 90 | 1.00 | Cetearyl alcohol |
| Crodamol STS | 1.00 | PPG-3 Benzyl Ether Myristate |
| DC 200 5 cps | 2.50 | Dimethicone |
| Crodamol TN | 1.50 | Isotridecyl Isononanoate |
| Phase D | | |
| Active ingredient comprising 200 ppm of Lipo-Phosphomalate of the invention | 3.00 | / |
| Phase E | | |
| Idealift ® | 4.00 | / |
| Phase F | | |
| Potassium sorbate | 0.10 | Potassium Sorbate |
| Phase G | | |
| NaOH 30% | 0.40 | Sodium hydroxide |
| H₂O | 4.00 | Water |
| Phase H | | |
| Orchid perfume | 0.10 | Fragrance |

Operating Procedure:

Stage 1: Disperse the carbomer in water with stirring staro v=300 rpm. Allow it to swell 1 hour.

Stage 2: Mix phase B.

Stage 3: Then add phase B in phase A. Homogenise. Heat in a water bath at 75° C.

Stage 4: Weigh phase C, mix and heat at 75° C. in the water bath.

Stage 5: Add phase D in the preceeding phase.

Stage 6: Add phase E in phase A+B.

Stage 7: Add phase C+D in phase A+B+E, with stirring staro v=300 rpm.

Stage 8: Then add phase F in the preceeding phase, with stirring staro v=300 rpm. Allow it to hoogenise 1 hour.

Stage 9: Neutralise with phase G with stirring staro v=500 rpm around 50° C.

Stage 10: Then add phase H around 55° C., homogenise thoroughly.

5/In Vivo Evaluation Results on Hydration

Principle:

Studies to demonstrate the in-vivo efficacy of the Lipo-Phosphomalate compound of the invention were carried out on two subject panels: a female panel and a male panel.

Several complementary methods were associated during this study:

Study of the improvement in skin hydration by stimulating the synthesis of natural wetting agents: Corneometer® and Moisturemeter-D™; Study of the remanant effect after one week.

Evaluation of the improvement of the homeostatis of the protective barrier by measuring transepidermal water loss (TEWL) on the Vapometer® and by the monitoring of the wetting power.

Evaluation of the improvement in the water homeostasis process via the assay of caspase-14 and glycerol. Ex-vivo method on adhesives.

Protocol:

Inclusion and Exclusion Criteria Specific to the Study:

Women and men with dry skin or skin prone to dryness were included. The women had to present constant hormone levels for 3 months preceding the test and during the test. Only cosmetic products provided during the study were to be used. The application of treatments was, therefore, prohibited two weeks before the study and for the duration of the study.

Types of Studies and Duration:

Two studies were conducted under single-blind using non-invasive methods vs. a placebo site; each volunteer thus acted as its own control.

A first short study of 21 conducted on 17 volunteers (mean age 44 years [19 to 61 years]).

A second, longer, of 2 months, conducted on 38 volunteers (mean age 47 years [19 to 68 years]).

Each panel were given a cream according to above example 4.2 and its respective placebo cream, that were massaged into one side of the face twice a day for a set period.

For the Vapometer® and wettability tests, the cream was applied to a forearm and the placebo cream to the opposite arm.

The study synopsis can be summarised according to the following diagram:

T0: Corneometer®, Moisturemeter™, Vapometer®, Skin wettability;

T 21 days: Corneometer®, Moisturemeter™;

T 2 months: Corneometer®, Moisturemeter™, Vapometer®, Skin wettability;

T 2 months+1 week: Corneometer®, Moisturemeter™.

Evaluation of Hydration

Hydration measurements were recorded using two complementary devices: the Corneometer® CM825 (Courage & Khazaka) and the MoistureMeter-D™ (Delfin). Both devices use the electrical properties of the ski and record an impedance measurement directly related to the water content of the skin. They provide information at various depths in the skin.

In each of these techniques, the signal recorded decreases very quickly with depth. Thus, the stratum corneum and superficial epidermis are mostly explored with the Corneometer®, which in theory, can record to a maximum depth of 100 μm. Similarly, the superficial epidermis and deep epidermis tend to be explored with the MoistureMeter-D™ (probe XS5), which nevertheless has a theoritical maximum depth of 500 μm.

A first measure was initially carried out to assess the restructuring and re-balancing effect of the Lipo-Phosphomalate on the face.

The measurements after 21 days were taken one night after the last application. Table 15 show the marked effect of the cream containing the Lipo-Phosphomalate compared to the placebo cream this only after 21 days of application.

TABLE 15

Improvement in skin homeostasis, measurements with the Corneometer ®, following application of the cream containing the Lipo-Phosphomalate on the face. (Mean values recorded on N = 17 volonteers, n = 3 measurements/volonteer)

| | T0 | | T 21 days | |
|---|---|---|---|---|
| | Cream containing 5.1 ppm of Lipo-Phosphomalate | PLACEBO | Cream containing 5.1 ppm of Lipo-Phosphomalate | PLACEBO |
| Mean | 46.24 ± 7.96 | 45.10 ± 8.97 | 49.04 ± 15.22 | 42.43 ± 17.04 |
| Mean of the differences | 1.14; nsd | | 6.61; p < 0.02 | |
| Changes (%) (→ max*) | +2.5% | | +15.6% (→ 48.4%) | |
| Differences between the cream of the invention/Placebo | | +13.1%; p < 0.04 (→ 44.6%) | | |

*Max: mean of the 9 best responders
nsd: non significant difference; Student's t test Hydration of the first layers of the stratum corneum of the face, measured with the Corneometer®, varied significantly by 13.1% on average between the zones with the Lipo-Phosphomalate containing cream and the zones with the placebo cream (p<0.04); this variation reached +44.6% for the 9 best responders.

A significant increase in hydration was also recorded with the MoistureMeter-D™ on the side of the face treated with Lipo-Phosphomalate containing cream of the invention; this increase was almost 17% (p<0.05 compared to placebo) with the variation reaching +44.0% for the 9 best responders.

TABLE 16

Improvement in skin homeostasis measured with the MoistureMeter-D ™, following application of the cream containing the Lipo-Phosphomalate of the invention on the face (Mean values on N = 17 volonteers, n = 3 mesurements/volonteer)

| | T0 | | T 21 days | |
|---|---|---|---|---|
| | Cream containing 5.1 ppm of Lipo-Phosphomalate | PLACEBO | Cream containing 5.1 ppm of Lipo-Phosphomalate | PLACEBO |
| Mean | 35.30 ± 9.32 | 36.08 ± 8.88 | 38.88 ± 9.67 | 33.98 ± 11.69 |
| Difference Cream of the invention/Placebo* | −0.78; nsd | | 4.90; p < 0.02 | |
| Change (%) Cream of the invention/Placebo (→ max*) | −2.2% | | +14.40% (→ 41.5%) | |
| Differences | | +16.6%, p < 0.02 (→ 44.0%) | | |

*Max: mean of the 9 best responders
nsd: non significant difference; Student's t test For the long term study over two months, as previously, measures were taken one night after the last application. The results with the Corneometer® confirm the positive trend already obtained with the short study; moreover, these results show that mean hydration of the face is highly increased on the side of the cream according to the invention compared to the placebo. Thus, for the panel as a whole (N=38), the increase between T0 and T2 months is of the order of +30.4%, this increase being highly significant (p<0.01) compared to the placebo which did not vary during this interval. This variation reached +58.0% for the 19 best responders.

Remarkably, the results show that, in men, the increase between T0 and T2 months was +38.4% on average (p<0.01 compared to the placebo; table 17). This variation amounted +59.0% for the 9 best responders.

TABLE 17

Improvement in skin homeostasis measured with the Corneometer ®, following application on the face of the cream of the invention containing the Lipo-Phosphomalate (mean values on N = 38 volonteers* including 16 men (♂), n = 3 mesurements/volonteer)

|  | T0 | | T 2 months | |
| --- | --- | --- | --- | --- |
|  | Cream containing 5.1 ppm of Lipo-Phosphomalate | PLACEBO | Cream containing 5.1 ppm of Lipo-Phosphomalate | PLACEBO |
| Mean* | 40.93* ± 8.93 | 43.02* ± 8.28 | 54.03* ± 12.78 | 43.04* ± 10.51 |
| Difference* Cream containing the Lipo-Phosphomalate/ Placebo | −2.09* and −2.46 (♂) | | 10.98* and 14.33 (♂) | |
| Change (%) Cream containing the Lipo-Phosphomalate/ Placebo (→ max) | −4.9%; nsd* and −5.7% (♂); nsd | | +25.5%; p < 0.01* (→ 52.8) and +32.8% (♂), p < 0.01 (→ 57.0) | |
| Differences | | +30.4%; p < 0.01* (→ 58.0) and +38.4% (♂); p < 0.01 (→ 59.0) | | |

*N = 38; nsd: non significant difference; Student's t test
→ Max: mean of the best responders To complement this, the measurements realised more in depth with the MoistureMeter-D™ show similar tendency. As a matter of fact, with the cream containing the Lipo-Phosphomalate, hydration of the face is highly increased in the whole panel (+28.6%; p<0.01). This variation reaches +48.5% for the 19 best responders.

As previously, the increase is here also greater for the males (+34.3%; p<0.01) compared to the placebo which changed insignificantly. This variation reaches +53.6% for the 9 best responders (table 18).

TABLE 18

Improvement in skin homeostasis measured with the MoistureMeter-D™ after applying the cream containing the Lipo-Phosphomalate on the face (Mean values on N = 38 volonteers including 16 men (♂), n = 3 measurements/volonteer)

|  | T0 | | T 2 months | |
| --- | --- | --- | --- | --- |
|  | Cream containing 5.1 ppm of Lipo-Phosphomalate | PLACEBO | Cream containing 5.1 ppm of Lipo-Phosphomalate | PLACEBO |
| Mean | 40.11 ± 7.40 | 40.89 ± 7.89 | 49.48 ± 9.02 | 39.04 ± 8.74 |
| Difference* Cream containing the lipo-phosphomalate/ Placebo | −0.78* and −1.63 (♂) | | 10.44* and 12.4 (♂) | |
| Change (%) Cream containing the lipo-phosphomalate/ Placebo | −1;9%*; nsd and −3.9% (♂); nsd | | 26.7%*; p < 0.01 (→ 46.8%) and 30.3% (♂); p < 0.01 (→ 48; 2%) | |
| Differences | | 28.6%*; p < 0.01 (→ 48.5%) and 34.3% (♂); p < 0.01 (→ 53.6%) | | |

*N = 38; non significant difference; Student's t test
→ Max: mean of the best responders These results clearly show that the trend observed at 21 days with the cream containing the Lipo-Phosphomalate of the invention was thre intensified after 2 months. Skin homeostasis of the volunteers, as shown in the hydration protocol, one night after the final application, is increased. The epidermis therefore seems to have acquired a reservoir of moisturizing or wetting agents, which is not linked to the composition of the cream since no change was observed on the placebo side.

Remanence Study

One week after the last application, a new measurement was recorded in a part of the volunteer panel (n=27 volonteers, 16 women and 11 men). The results obtained with the Corneometer® and the MoistureMeter-D™ show the remarkable resistance to drying out recorded for the site treated with the cream containing the Lipo-Phosphomalate of the invention compared to the placebo (tables 19 and 20).

TABLE 19

Remnant of the improvement of cutaneous homeostasis of the face after one week without application, measured with the Corneometer ®. (mean values on N = 27 volonteers, n = 3 mesurements/volonteer)

| | T0 | | T 2 months | | T 2 months + 1 week | |
|---|---|---|---|---|---|---|
| | Cream containing 5.1 ppm of Lipo-Phosphomalate | PLACEBO | Cream containing 5.1 ppm of Lipo-Phosphomalate | PLACEBO | Cream containing 5.1 ppm of Lipo-Phosphomalate | PLACEBO |
| Mean | $42.23 \pm 9.08$ | $43.00 \pm 8.17$ | $57.89 \pm 12.16$ | $44.12 \pm 11.07$ | $47.30 \pm 12.97$ | $42.65 \pm 11.44$ |
| Difference Cream containing the lipo-phosphomalate vs. Placebo | $-0.7$; nsd | | $+13.77$; $p < 0.01$ | | $+4.64$; $p < 0.01$ | |
| % change Cream containing the lipo-phosphomalate vs. Placebo | $-1.8\%$ | | $+31.2\%$ | | $+10.9\%$ ($\rightarrow +24.5\%$)* | |
| % change T 2 months + 1 week vs. T0 | | | $+12.7\%$; $p < 0.01$ ($\rightarrow +27.1\%$)* | | | |

( )*½ panel = 14 best responders.

TABLE 20

Remnant of the improvement of cutaneous homeostasis of the face after one week without application, measured with the MoistureMeter-D ™ (mean values on N = 27 volonteers, n = 3 mesurements/volonteer)

| | T0 | | T 2 months | | T 2 months + 1 week | |
|---|---|---|---|---|---|---|
| | Cream containing 5.1 ppm of Lipo-Phosphomalate | PLACEBO | Cream containing 5.1 ppm of Lipo-Phosphomalate | PLACEBO | Cream containing 5.1 ppm of Lipo-Phosphomalate | PLACEBO |
| Mean | $40.82 \pm 7.55$ | $41.56 \pm 6.85$ | $50.81 \pm 8.66$ | $39.59 \pm 8.50$ | $44.80 \pm 8.60$ | $36.48 \pm 8.07$ |
| Difference Cream containing the lipo-phosphomalate vs. Placebo | $-0.75$; nsd | | $11.23$; $p < 0.01$ | | $8.32$; $p < 0.01$ | |
| % change Cream containing the lipo-phosphomalate vs. Placebo | $-1.8\%$ | | $+28.4\%$ | | $22.8\%$ ($\rightarrow 34.7\%$)* | |
| T 2 months + 1 week vs. T0 | | | $+24.6\%$; $p < 0.01$ ($\rightarrow +35.2\%$)* | | | |

( )*½ panel = 14 best responders.

The results show that the cream containing the Lipo-Phosphomalate of the invention triggers a very interesting residual effect after one week without application. Skin hydration is thus maintained at a high level (+23%, $p<0.01$ in all volunteers on the panel and +35% ($p<0.01$) for half of the panel).

Evaluation of Homeostasis of the Hydrolipid Barrier

Strengthening of the barrier was assessed from 2 different perspectives:
- A dynamic evaluation of the barrier by a measuring of the transepidermal water loss following a stripping-induced rupture in the barrier.
- A visual evaluation of the barrier by measuring its wettability.

Mesurement of TEWL

The establishing and maintaining of the hydrolipid skin barrier are essential for the organism. In the assay reported below, the re-establishment of this barrier was assessed after rupture triggered by repeated strippings.

At T0, transepidermal water loss (or TEWL) of the forearm was measured using the Vapometer® (Delfin), a device using a closed chamber. A series of strippings was then carried out in a controlled manner in an attempt to slightly disrupt barrier homeostasis. The destruction-mediated increase in TEWL was measured at steady-state. This method allows barrier resistance to be evaluated.

After applying the cream containing the Lipo-Phosphomalate of the invention or the placebo cream, a protocol identical to the one used on T0 was followed. This facilitated the evaluation of a potential improvement in resistance.

Table 21: Mean increase in TEWL following disrupted homeostasis (Mean values recorded in N=38 volonteers, n=3 mesurements/volonteer).

Conversely, after 2 months's treatment, the responses were very different depending on the product tested.

As to the placebo, the rupture in homeostasis was less pronounced than at T0, mainly due to the massage effect, but the increase in TEWL was nevertheless high (3.40 units), i.e. a difference of 2.96 units compared to T0.

With the cream containing the Lipo-Phosphomalate of the invention, the destruction at 2 months caused only a slight rupture in homeostasis (1.70 unit), with a gain of 5.03 compared to T0. The difference between the two cases is very significant and in favour of the cream according to the invention. The cream according to the invention improves the barrier of +54.2% ($p<0.01$).

Wettability Measurement

An original measurement of the condition of the skin barrier can be obtained by measuring the wettability of the skin. A drop of water deposited on the skin can interact with the skin in a totally different manner depending on the condition and, therefore, the composition, of the barrier.

From a physico-chemical standpoint, one drop deposited on the skin will spread only slightly if the skin is hydrophobic (dry, atopic skin, lipid-depleted due to soaps). Its wettability is said to be poor. Conversely, an improvement in the quality of the stratum corneum improves the wettability of the skin.

Using this property, we deposited a microdrop of water (10 μL) in a reproductible manner on the skin and measured its ability to spread using a video microscope (Scalar) and image analysis software. Although imperfect because it was less detailed than contact angle measurements and similarly less accurate, measurement of the surface area occupied by the drop of water on the skin was nevertheless a good indicator of skin wettability.

TABLE 21

Mean increase in TEWL following disrupted homeostasis (Mean values recorded in N = 38 volonteers, n = 3 mesurements/volonteer).

| | T0 | | T 2 mois | |
|---|---|---|---|---|
| | Cream containing 5.1 ppm of Lipo-Phosphomalate | PLACEBO | Cream containing 5.1 ppm of Lipo-Phosphomalate | PLACEBO |
| Loss of homeostasy (in $g/m^2/h$)* | 6.63 ± 5.00 | 6.36 ± 4.60 | 1.70 ± 1.50 | 3.40 ± 2.5 |
| Difference* Cream containing the Lipo-Phosphomalate/ Placebo cream | +0.27 | | −1.70 | |
| Change (%) Cream containing the Lipo-Phosphomalate/ Placebo cream | −4.2%**; nsd | | +50%**; $p<0.01$ | |
| % change T 2 months vs. T0 | | +54.2%; $p<0.01$ | | |

*Mean differences in TEWL between before and after rupture by strippings.

**100 × (Placebo-cream of the invention)/Placebo; nsd: non significant difference; Student't test The destruction at T0 increased the TEWL by approximately 6.5 units on both the site of the cream according to the invention and on the placebo site is observed (i.e. homeostasis rupture).

TABLE 22

Mean variation in the wettability of a drop on the forearm following application of the cream containing the Lipo-Phosphomalate of the invention (Mean values recorded in N = 37 volonteers, n = 3 mesurements/volonteer).

|  | Cream containing 5.1 ppm of Lipo-Phosphomalate | | PLACEBO | |
| --- | --- | --- | --- | --- |
|  | T0 | T 2 months | T0 | T 2 months |
| Occupied surface ($mm^2$) | 9.73 ± 2.80 | 13.03 ± 7.70 | 10.74 ± 4.3 | 12.73 ± 6.6 |
| Gain vs. T0 (in %) |  | +33.9% |  | +18.5% |
| Significance vs. T0 |  | p < 0.05 |  | nsd | nsd: non significant difference; Student't test

As the results show, the surface occupied by the drop significantly increased by +33.9% (p<0.05) on the site treated with the cream containing the Lipo-Phosphomalate, thus indicating better wettability. This shows that the hydrolipid film is thicker. The placebo site also exhibits increased wettability but which remains not significant. The placebo cream probably supplied the outer layers of the stratum corneum with certain emollient properties, which affected the wettability result.

Evaluation of the Homeostasis of the Wetting Agents

The restoration evaluation of a better balance within the stratum corneum was evaluated by measuring two of the key factors obtained by strippings:

Evaluation of caspase-14 activity,

Evaluation of endogenous glycerol production.

Given the large number of samples (strippings) to be collected, these evaluations were carried out solely using a male panel of 15 volunteers.

Caspase-14 Assay

We saw in the in vitro section, that the Lipo-Phosphomalate of the invention induced gene expression and caspase-14 synthesis in cultured keratinocytes and reconstructed epidermis. We have developed an original method for assaying the activity of this enzyme from strips collected from the forearms of volunteers. These strips (6 DSquame® in total) underwent extraction in a neutral pH buffer. This solution was then placed in contact with a synthetic substrate cleaved by caspase-14; the fluorescence resulting from this process was recorded using a fluorescence reader.

TABLE 23

Assay of the activity of caspase-14 extracted from strips taken from forearm (Mean values for N = 15 volonteers, 6 strips/volonteer)

|  | T0 | | T 2 months | |
| --- | --- | --- | --- | --- |
|  | Cream containing 5.1 ppm of Lipo-Phosphomalate | PLACEBO | Cream containing 5.1 ppm of Lipo-Phosphomalate | PLACEBO |
| Mean activity (UFA/min/µg of proteins) | 89.6 ± 37.3 | 86.0 ± 43.2 | 167.5 ± 71.5 | 120.5 ± 39.8 |
| Mean of the differences |  | +3.6; nsd |  | +47.0; p < 0.02 |
| Changes (in %) |  | +4.2% |  | +39.0% |
| Differences cream of the invention/Placebo |  |  | +34.8% |  | nsd: non significant difference; Student't test

These results show that the activity of caspase-14 is incrased on average by +34.8% on the side treated with the cream containing the Lipo-Phosphomalate compared to the placebo side (p<0.02). The increase in this activity in the upper layers of the stratum corneum highlights the increase in the production of this enzyme observed in molecular biology and immunofluorescence.

Endogenous Glycerol Assay

In parallel to the caspase-14 assay, we used the same extracts to evaluate the quantity of glycerol present in the upper layers of the epidermis before and after application of the cream containing the Lipo-Phosphomalate of the invention or the placebo cream. This method allows free glycerol to be assayed thanks to the cascade of enzymatic reactions, finally giving a coloured reaction, which was assayed at 540 nm.

TABLE 24

Assay of glycerol extracted from strips taken from the foerarms
(Means values recorded in N = 15 volonteers, 6 strips/volonteer)

|  | T0 | | T 2 months | |
| --- | --- | --- | --- | --- |
|  | Cream containing 5.1 ppm of Lipo-Phosphomalate | PLACEBO | Cream containing 5.1 ppm of Lipo-Phosphomalate | PLACEBO |
| Glycerol mean (nmol/μg of proteins) | 0.164 ± 0.115 | 0.169 ± 0.135 | 1.128 ± 0.641 | 0.266 ± 0.177 |
| Mean of the differences | −0.005; nsd | | +0.862; p < 0.01 | |
| Changes (%) | −3% | | +325% | |
| Differences cream of the invention/ Placebo | | +328% | | | nsd: non significant difference; Student't test

These results show that the quantity of glycerol found in the stratum corneum increased by +328% on average on the side to which the cream containing the Lipo-Phosphomalate was applied compared to the placebo side (p<0.01).

The quantities detected are consistent with those given in the literature. The increase in this component, which is essential for skin hydration, is linked to the inductin observed in molecular biology of the LIPE lipase known to hydrolyse triacylglycerols, mono- and diglycerides as well as cholesterol esters in keratinocytes; this lipase would, therefore allow the salting out of glycerol in the cell and its subsequent accumulation in the corneocytes.

All these results recorded in volunteers who applied the cream containing the Lipo-Phosphomalate or the placebo cream show that the cream containing the Lipo-Phosphomalate can boost water homeostasis in the skin by promoting the synthesis of compounds essential for this homeostasis. Thus filaggrin and its key enzymes such as caspase-14 provide the cell with its wetting agents of protein origin. Moreover, complex lipids such as ceramides or cholesterol, which establish the barrier function, care increased. Finally, a rise in intra-cornocytic glycerol—a component with strong wetting properties—completes the picture.

The invention claimed is:

1. A compound represented by Formula I:

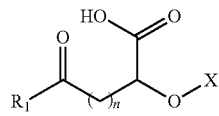

wherein:

$X = PO(OH)_2$ or $SO_2(OH)$ $R_1 = OR_2$ or $NR_3R_4$ $R_2$ is a hydrocarbon chain having at least 4 carbon atoms $R_3$ and $R_4$ are, independently from each other, either a hydrogen atom or an $R_2$ chain, wherein at least one of $R_3$ and $R_4$ are an $R_2$ type chain $n = 1$.

2. A compound according to claim 1, wherein $R_1 = OR_2$.

3. A compound according to claim 1, wherein $X = PO(OH)_2$.

4. A compound according to claim 1, wherein the compound is obtained from malic acid or from one of its derivatives or analogs.

5. A compound according to claim 1 represented by Formula IV

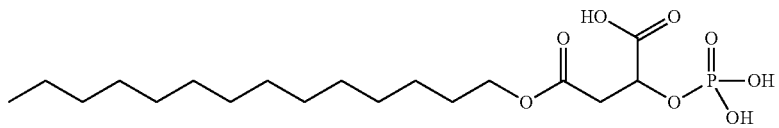 [SMILES: CCCCCCCCCCCCCCOC(=O)CC(OP(=O)(O)O)C(=O)O]

6. A composition comprising:
1) a compound represented by Formula I:

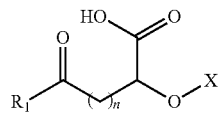

wherein:
X=PO(OH)$_2$ or SO$_2$(OH)
R$_1$=OR$_2$ or NR$_3$R$_4$
R$_2$ is a hydrocarbon chain having at least 4 carbon atoms
R$_3$ and R$_4$ are, independently from each other, either a hydrogen atom or an R$_2$ chain, wherein at least one of R$_3$ and R$_4$ are an R$_2$ type chain
n=1; and
2) a physiologically acceptable medium.

7. A method of topically applying the composition according to claim 6 for improving the general condition of the skin.

8. A method of topically applying the composition according to claim 6 for the prevention or treatment of the cutaneous signs of aging.

9. A method of topically applying the composition according to claim 6 for the prevention or treatment of cutaneous dehydration.

10. A method of topically applying the composition according to claim 6 for the prevention or treatment of fine lines and wrinkles.

11. A method of topically applying the composition according to claim 6 for the prevention or treatment of loss of firmness of the skin.

12. A method of topically applying the composition according to claim 6 for improving the suppleness of skin.

13. A method of topically applying the composition according to claim 6 for stimulating the expansion of adipose tissue of the skin.

14. A method of topically applying the composition according to claim 6 for lightening the skin.

15. The composition according to claim 6, further comprising at least one additional cosmetic active selected from lightening agents, anti-redness agents, sunscreens, moisturizers, humectants, exfoliants, anti-aging agents, anti-wrinkle and anti-fine line agents, agents that stimulate collagen and/or elastin synthesis, volumizing agents, agents that improves elastic properties, anti-acne agents, anti-inflammatory agents, anti-oxidants, anti-free radical agents, propigmenting agents, depigmenting agents, depilatories, anti-regrowth or growth promoting agents, peptides, and vitamins.

16. The composition according to claim 15, wherein the additional cosmetic active is selected from vitamin compounds, more particularly vitamin B3 compounds like niacinamide or tocophérol, retinoid compounds like retinol, hexamidin, α-lipoic acid, resveratrol, DHEA or N-acetyl-Tyr-Arg-O-hexadecyl, Pal-VGVAPG (SEQ ID NO:7), Pal-KTTKS (SEQ ID NO:8), Pal-GHK, Pal-KMO2K and Pal-GQPR (SEQ ID NO:9) peptides.

* * * * *

```
                         SEQUENCE LISTING

<160> NUMBER OF SEQ ID NOS: 11

<210> SEQ ID NO 1
<211> LENGTH: 4
<212> TYPE: PRT
<213> ORGANISM: Artificial
<220> FEATURE:
<223> OTHER INFORMATION: synthetic peptide

<400> SEQUENCE: 1

Arg Ser Arg Lys
1

<210> SEQ ID NO 2
<211> LENGTH: 4
<212> TYPE: PRT
<213> ORGANISM: Artificial
<220> FEATURE:
<223> OTHER INFORMATION: synthetic peptide

<400> SEQUENCE: 2

Gly Gln Pro Arg
1

<210> SEQ ID NO 3
<211> LENGTH: 4
<212> TYPE: PRT
<213> ORGANISM: Artificial
<220> FEATURE:
<223> OTHER INFORMATION: synthetic peptide

<400> SEQUENCE: 3
```

```
Lys Thr Phe Lys
1

<210> SEQ ID NO 4
<211> LENGTH: 5
<212> TYPE: PRT
<213> ORGANISM: Artificial
<220> FEATURE:
<223> OTHER INFORMATION: Synthetic peptide

<400> SEQUENCE: 4

Lys Thr Thr Lys Ser
1               5

<210> SEQ ID NO 5
<211> LENGTH: 6
<212> TYPE: PRT
<213> ORGANISM: Artificial
<220> FEATURE:
<223> OTHER INFORMATION: synthetic peptide

<400> SEQUENCE: 5

Gly Lys Thr Thr Lys Ser
1               5

<210> SEQ ID NO 6
<211> LENGTH: 6
<212> TYPE: PRT
<213> ORGANISM: Artificial
<220> FEATURE:
<223> OTHER INFORMATION: Synthetic peptide

<400> SEQUENCE: 6

Val Gly Val Ala Pro Gly
1               5

<210> SEQ ID NO 7
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description
      Pal-Val-Gly-Val-Ala-Pro-Gly.

<400> SEQUENCE: 7

Val Gly Val Ala Pro Gly
1               5

<210> SEQ ID NO 8
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description Pal-Lys-
      Thr-Thr-Lys-Ser

<400> SEQUENCE: 8

Lys Thr Thr Lys Ser
1               5

<210> SEQ ID NO 9
```

```
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description Pal-Gly-
      Gln-Pro-Arg

<400> SEQUENCE: 9

Gly Gln Pro Arg
1

<210> SEQ ID NO 10
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description Pal-Tyr-
      Gly-Gly-Phe-Met

<400> SEQUENCE: 10

Tyr Gly Gly Phe Met
1               5

<210> SEQ ID NO 11
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, Pal (C16). Seq description Pal-Tyr-
      Gly-Gly-Phe-Leu

<400> SEQUENCE: 11

Tyr Gly Gly Phe Leu
1               5
```